(12) United States Patent
Weissig et al.

(10) Patent No.: US 7,279,326 B2
(45) Date of Patent: Oct. 9, 2007

(54) COMPOSITION FOR DELIVERY OF A MITOCHONDRIAL GENOME TO A CELL

(75) Inventors: Volkmar Weissig, Nashua, NH (US); Vladimir Torchilin, Charlestown, MA (US)

(73) Assignee: Northeastern University, Boston, MA (US)

( * ) Notice: Subject to any disclaimer, the term of this patent is extended or adjusted under 35 U.S.C. 154(b) by 478 days.

(21) Appl. No.: 10/485,407

(22) PCT Filed: Jul. 31, 2002

(86) PCT No.: PCT/US02/24179

§ 371 (c)(1), (2), (4) Date: Jan. 30, 2004

(87) PCT Pub. No.: WO03/012050

PCT Pub. Date: Feb. 13, 2003

(65) Prior Publication Data
US 2004/0192627 A1 Sep. 30, 2004

Related U.S. Application Data

(60) Provisional application No. 60/309,000, filed on Jul. 31, 2001.

(51) Int. Cl.
*C12N 15/00* (2006.01)
(52) U.S. Cl. .................. 435/320.1; 435/455
(58) Field of Classification Search ............. 435/320.1, 435/455; 514/44; 424/93.2
See application file for complete search history.

(56) References Cited

U.S. PATENT DOCUMENTS

| | | | |
|---|---|---|---|
| 5,939,318 A | 8/1999 | Miller et al. | 435/325 |
| 6,090,619 A * | 7/2000 | Weissig et al. | 435/320.1 |
| 6,171,863 B1 * | 1/2001 | Weissig et al. | 435/458 |
| 6,627,618 B2 * | 9/2003 | Weissig et al. | 514/44 |

OTHER PUBLICATIONS

Weissig et al. Binding and Release of DNA-Peptide Conjugates by Cationic Mitochondriotropic Vesicles (DQAsomes). Proceed. International Symp. Controlled Release Bioactive Materials. 2001, vol. 28, pp. 850-851.*

Seibel et al. Transfection of Mitochondria: Strategy Towards a Gene Therapy of Mitochondria DNA Diseases. Nucleic Acids Res. 1995, vol. 23, pp. 10-17.*

Weissig, D'Souza and Torchilin. DQAsomes/DNA Complexes Release DNA Upon Contact With Isolated Mouse Liver Mitochondria. J. Controlled Release. 2001, vol. 75, pp. 401-408.*

Chinnery et al. Epidemiology and Treatment of Mitochondrial Disorders. American J. Medical Genetics (Semin. Med. Genet.). 2001, vol. 106, pp. 94-101.*

Torchilin et al. Intracellular Targets for DNA Delivery: Nuclei and Mitochondria. Somatic Cell Molec. Genetics. Nov. 2002, vol. 27, pp. 49-64.*

Weissig et al., "Lipofection with DQAsomes: Mitochondria-Specific?" Proceed. Int'l. Symp. Control. Rel. Bioact. Mater., 25 (1998) Controlled Release Society, Inc., pp. 180-181.

Weissig, et al., "DQAsomes: A Novel Potential Drug and Gene Delivery System Made from Dequalinium", Pharmaceutical Resrarch, vol. 15, No. 2, 1998, pp. 334-337.

Weiss, et al., "Dequalinium, a topical antimicrobial agent, displays anticarcinoma activity based on selective mitochondrial Accumulation", Proc. Natl. Acad. Sci. USA, vol. 84, pp. 5444-5448, Aug. 1987, Medical Sciences.

Zhuo, et al., Inhibition and Photoinactivation of the Bovine Heart Mitochondrial $F_1$-ATPase By The Cytotoxic Agent, Dequalinium, vol. 152, No. 3, 1988, pp. 968-972.

* cited by examiner

*Primary Examiner*—Deborah Crouch

(74) *Attorney, Agent, or Firm*—Weingarten, Schurgin, Gagnebin & Lebovici LLP

(57) ABSTRACT

The invention provides composition and methods for delivering a composition according to the invention comprising a wild-type (wt) mitochondrial DNA (mtDNA) molecule to a mammalian cell. The wt-mtDNA molecule is a functional mtDNA molecule that includes the entire mitochondrial genome. The wt-mtDNA molecule in the composition of the invention has a mitochondrial leader sequence (MLS) peptide attached to facilitate the uptake of the mtDNA molecule into a mitochondrion of the mammalian cell. The delivery of the wt-mtDNA/MLS peptide complex is used as a general replenishment therapy for conditions attributed to mtDNA defects, independent of the specific defect in the mtDNA.

7 Claims, No Drawings

COMPOSITION FOR DELIVERY OF A MITOCHONDRIAL GENOME TO A CELL

CROSS REFERENCE TO RELATED APPLICATIONS

This application claims the benefit under 35 U.S.C. §119 (e) of U.S. Provisional Patent Application No. 60/309,000 filed on Jul. 31, 2001, entitled MITOCHONDRIAL GENOME REPLACEMENT, the whole of which is hereby incorporated by reference herein.

STATEMENT REGARDING FEDERALLY SPONSORED RESEARCH OR DEVELOPMENT

N/A

BACKGROUND OF THE INVENTION

The number of diseases found to be caused by defects of the mitochondrial genome has grown significantly over the last decade (Wallace et al., 1988; Holt et al., 1988; Harding et al., 1999; Papa et al., 1996; Wallace, 1999 and Pulkes et al., 2001). Organs affected by defects in the mitochondrial DNA (mtDNA) include the brain, skeletal muscle, heart, kidney and liver (De Vivo, 1993). Hence, neuromuscular and neurodegenerative diseases represent the two largest groups of mtDNA diseases. Also, prominent clinical signs often involve the visual system. Ptosis, restriction of eye movement, optic atrophy, pigmentary retinopathy, sudden or subacute visual loss, and hemianopia are particularly noteworthy (De Vivo, 1993). (See also www.neuro.wustl.edu/neuromuscular/mitosyn.html or www.gen.emory.edu/mitomap.html.) Despite major advances in understanding mtDNA defects at the genetic and biochemical level, however, there is no satisfactory treatment available for the vast majority of patients. This is due to the fact that any mtDNA mutation or deletion affects the final common pathway of oxidative metabolism in the mitochondria making it impossible to bypass the defect by administering alternative energy-carrying metabolites (Chrzanowska-Lightowler et al., 1995). These objective limitations of conventional biochemical treatment for patients with defects of mtDNA warrant the exploration of other gene therapeutic approaches.

BRIEF SUMMARY OF THE INVENTION

The compositions and methods according to the invention provide such a viable approach. The invention is directed to delivering a composition according to the invention comprising an entire wild-type mitochondrial DNA molecule to a mammalian cell. The wild-type mitochondrial DNA molecule in the composition of the invention has attached to it a mitochondrial leader sequence (MLS) peptide attached to facilitate the uptake of the mitochondrial DNA molecule into a mitochondrion of the mammalian cell. The delivery of the wild-type mitochondrial DNA molecule complexed with the MLS peptide is used as a general replenishment therapy for the treatment of conditions attributed to mitochondrial DNA (mtDNA) defects, independent of the specific defect.

In accordance with the invention, a "wild-type mitochondrial DNA molecule" is defined as the entire mitochondrial genome. The composition according to the invention preferably also comprises a carrier vehicle, which facilitates transport of the mitochondrial DNA molecule into the mammalian cell. Examples of suitable carrier vehicles include, but are not limited to, a cationic lipid, a viral vector, a non-viral vector or a mitochondriotropic vehicle, which specifically targets delivery of the composition to a mitochondrion of the cell.

DETAILED DESCRIPTION OF THE INVENTION

The invention provides a novel and effective approach for delivering a wild-type (wt) mitochondrial DNA (mtDNA) molecule to a mammalian cell and, particularly, to a mitochondrion of the cell. A composition according to the invention includes a wt-mtDNA molecule with an attached mitochondrial leader sequence (MLS) peptide for providing effective uptake into a mitochondrion.

The wt-mtDNA molecule in compositions according to the invention is useful for the treatment of conditions attributed to mitochondrial DNA defects, independent of the specific mutation in a patient's mitochondrial genome. The invention replenishes a mitochondrion (of a cell, tissue, or organism) bearing damaged mtDNA molecules with healthy mtDNA. For the appearance of clinical symptoms in cases of mtDNA damage, a certain amount of damaged mtDNA molecules need to accumulate within a mitochondrion, or cell, or tissue. In other words, a certain "threshold" in terms of mtDNA mutations needs to be crossed. By introducing wt-mtDNA into cells, one can shift the balance between mutated and wt-mtDNA towards healthy mtDNA.

Using wt-mtDNA as a therapeutic agent has also the significant advantage that its reduplication and propagation is governed by the same mechanism that applies to the patient's endogenous mtDNA. This will result in a further increase of the amount of healthy mtDNA, once delivered into the appropriate tissue. Unlike the problems that nuclear-based gene therapy is facing, the therapeutic mitochondrial gene (i.e., wt-mtDNA) does not need to be integrated into the cell's genome. It represents at the time of delivery an independent functioning mitochondrial genome. Once delivered into the cell's mitochondrion, it will act and function just like all other mtDNA molecules of the cell.

A "wt-mtDNA molecule" is defined as a functional mitochondrial DNA molecule and includes the entire mitochondrial genome. All mtDNA molecules are functionally interchangeable among humans; e.g.; the enzyme complexes for the respiratory chain that are encoded in the mtDNA are identical in all humans. Individual cells contain many mitochondria and each mitochondrion contains 2-10 copies of mtDNA (Satoh et al., 1991; Robin et al., 1988).

The mitochondrial genome is a circular double-stranded molecule, which consists of 16,569 base pairs. It contains 37 genes including 13 protein-encoding genes, 22 transfer RNA (tRNA) genes and two ribosomal RNA (rRNA) genes. The 13 protein-encoding genes are components of the mitochondrial respiratory chain. The wt-mtDNA molecule may also include sequence polymorphism, but it remains fully functional. (See Papa et al., 1996 and Pulkes et al., 2001.)

A wt-mtDNA molecule useful in the composition of the invention can be derived, e.g., from a mammalian cell or cell culture, cloned from an isolated wt-mtDNA molecule or synthesized using conventional techniques well known in the art. Such wt-mtDNA can even be isolated from healthy cells, tissues or organs of the individual patient who has a condition that is attributed to a mitochondrial defect. MtDNA mutations in a patient are not prevalent in all tissues and all cells to the same degree. Healthy mtDNA coexists with damaged mtDNA in the same organism, the same tissue, the same cell and even the same mitochondrion, which is a phenomena called "heteroplasmy." Isolation and purification of mtDNA (further described below) from, for example, spinner tissue culture cells may be performed using CsCl-equilibrium centrifugation as described by W. W. Hauswirth et al., 1987. The human suspension cell cultures may be derived from, for example, COLO-205 Colon Adenocarcinoma and MOLT-4 Acute Lymphoblastic Leukemia. Synthesis of a wt-mtDNA molecule may be performed using, for example, a DNA synthesizer such as ASM-700 DNA Synthesizer and ASM-800 DNA Synthesizer, both of which are sold by Biosset Ltd. (Novosibirsk, Russia), or a DNA or a DNA-Analog Synthesizer from Labtronix Inc. (Monroe, Oreg.).

The MLS peptide of the preferred embodiment of the invention is a specific peptide, recognized by components of the mitochondrial protein import machinery. While various MLS peptides may be used in the invention, preferably, the peptides would be one of the following: the presequence peptide of the nuclear-encoded human cytochroine c oxidase (COX) subunit VIII (MSVLTPLLLRGLTGSAR-RLPVPRAKIHSL) (Chinnery et al., 1999); the amino-terminal leader peptide of the rat ornithine transcarbamylase (OTC) (MLSNLRILLNKAALRKAHTSMVRN-FRYGKPVQC) (Seibel et al., 1995) may also be used; or the presequence of cytochrome oxidase subunit IV (MLSLRQ-SIRFFKPATRTL) (Alberts et al., 1994) Conventional protocols may be used to conjugate the wt-mtDNA with the MLS peptide, e.g., pGeneGrip™ technology (as further described below).

A carrier vehicle preferably is used to transport the wt-mtDNA molecule/MLS peptide complex into a cell. Alternatively, microinjection technology is used where a solution of wt-mtDNA/MLS peptide complex can be injected into a cell. Any carrier vehicle may be used that is suitable to deliver the wt-mtDNA molecule/MLS peptide complex into a mammalian cell. For example, carrier vehicles used for traditional gene therapy may be used. In one aspect, the carrier vehicle used in accordance with the invention can be a viral vector, a non-viral vector or a cationic lipid. (See Sobol et al., 1995; Rolland et al., 1999; Ledley, 1996; Gregoriadis, 2000.) Preferably, the carrier vehicle is a vehicle that specifically targets the mitochondrion of a mammalian cell, i.e., it is a "mitochondriotropic" carrier vehicle. In another aspect, the mitochondriotropic carrier vehicle is a non-viral gene therapy vector comprising a salt of dequalinium. Dequalinium is an amphiphilic dicationic compound that is symmetrical with two delocalized cationic centers separated by a relatively long hydrocarbon chain. The hydrocarbon chain may have, for example, from about 5 to about 20 carbons, and, preferably, the hydrocarbon chain may have from about 8 to about 12 carbons. An ordinary skilled artisan will appreciate that various salts of dequalinium can be used. (See Weissig et al., U.S. Patent Application Publication No. 2001/0001067, May 10, 2001.) This carrier vehicle, also known as DQAsome, is a mitochondrion-specific transfection vector, which facilitates the delivery of the therapeutic wt-mtDNA molecule/MLS peptide complex into mitochondria of living mammalian cells.

Amphiphilic cationic compounds with a delocalized charge center have been known to accumulate in mitochondria of living cells in response to the mitochondrial membrane potential. For an exemplary design of the mitochondriotropic carrier vehicle, the self-assembly behavior of dequalinium and its derivatives is used. These are mitochondriotropic amphiphiles resembling "bola"-form electrolytes. Such "bola"-form-like amphiphiles are able to form liposome-like cationic vesicles ("bolasomes"), which have been termed "DQAsomes" when prepared from dequalinium. It was shown that DQAsomes fulfill all essential prerequisites for a mitochondria-specific DNA delivery system. DQAsomes bind and condense mtDNA, protect mtDNA from DNAse digestion, mediate the cellular uptake of mtDNA and its transport into close proximity of mitochondria and do not release DNA when in contact with the surface of mitochondria. In addition, the presence of a leader sequence peptide attached to the DNA does not interfere with binding and release comparable to non-viral vectors already in clinical gene therapy trials.

Thus, the present invention solves the previously identified difficulties encountered in transporting useful portions of mtDNA into mitochondria of cells. Several techniques for the delivery of DNA into mitochondria of mammalian cells have been suggested. However, the methods are restricted to the use of isolated mitochondria that are outside the cells. Generally, two different approaches to mitochondrial gene therapy have been pursued in the art. The first approach is a direct mitochondrial gene therapy, which is based on the delivery of DNA fragments directly into mitochondria followed by transcription and translation inside this organelle. The other approach is an indirect mitochondrial therapy, which involves the expression of a wild-type copy of the defective mitochondrial gene in the nucleus, followed by cytoplasmic synthesis and subsequent targeting of the gene product to the mitochondria, employing mitochondrial leader peptides.

Numerous viral and non-viral DNA delivery vectors are available for the transport of exogenous DNA into the nucleus (reviewed in Sobol et al., 1995; Rolland et al., 1999; Ledley, 1996 and Gregoriadis, 2000) therefore making the indirect approach very attractive. However, the adoption of the nuclear-cytosolic pathway for indirect mitochondrial gene therapy requires combating four major problems:

Firstly, the mitochondrial genetic code in mammals differs from the universal code in four codons (Barrell et al., 1979): UGA (Stop→Trp), AUA (Ile→Met), AGA (Arg→Stop) and AGG (Arg→Stop). In addition, Sewards et al. demonstrated that the mitochondrial heavy-strand promoter is unable to function as a promoter in nuclear DNA, supporting the view that nuclear and mitochondrial transcription systems in human cells are functionally independent (Sewards et al., 1994). Thus, a claim that the functional expression of a reporter gene, either via the nuclear-cytosolic or the mitochondrial pathway, depends only on the final subcellular localization of the gene, seems very unlikely (see Conary et al., 1995).

Secondly, the majority of mtDNA defects involve transfer RNAs (tRNAs). While evidence has been presented for the transport of nucleus-encoded tRNA into mitochondria in diverse organisms, such as plants, yeast and protozoa (Schneider et al., 1994), so far no natural mechanism for the mitochondrial uptake of cytosolic tRNAs in mammalian cells has been reported.

Thirdly, it is generally agreed that the thirteen proteins encoded for by mtDNA are extremely hydrophobic peptides, which would not be readily imported by the mitochondrial protein import machinery (Scheffler, 1999) and, therefore, need to be synthesized at the location of their function. Such hydrophobicity-caused prevention of mitochondrial protein import was most recently demonstrated by Owen et al., 2000. These authors have designed recombinant adeno-associated virus constructs to express the reporter gene encoding green fluorescent protein (GFP), fused to a targeting presequence that directed GFP to be translocated into mitochondria. These vectors mediated expression of mitochondrial-localized GFP, as indicated by fluorescence microscopy and electron microscopy, in respiring human embryonic kidney 293 cells and non-respiring mtDNA-deficient cells. Yet, when sequences encoding hydrophobic segments of proteins normally encoded by mtDNA were inserted between the presequence and GFP, mitochondrial import failed to occur. It was concluded that the hydrophobicity of mtDNA-encoded proteins limits their ability to be transported from the cytoplasma.

Nevertheless, the 13 mitochondrial coded proteins are not equally hydrophobic which makes allotopic expression, i.e., cytosolic translation followed by mitochondrial import, of at least some of them feasible (deGray, 2000). The proof of concept of this approach was provided by Nagley et al. (1988) who demonstrated in 1988 the phenotypic rescue of a mutation in yeast ATPase subunit eight by a plasmid-borne nuclear transgene, which was re-coded to compensate for the difference between the human nuclear and mitochondrial genetic code. Most recently, Steven J. Zullo and Jerome M. Eisenstadt have succeeded in the functional allotopic expression of ATPase subunit 6 in Chinese hamster ovary cells and in human cybrids that are homoplasmic for the NARP (T8993G) ATPase 6 mutation thus demonstrating for the first time the feasibility of allotopic expression (i.e., indirect mitochondrial gene therapy) in mammalian cells.

As an approach for overcoming the un-importabilty of highly hydrophobic mitochondrial polypeptides the allotopic expression of which appears as unachievable, protein-splicing elements, so-called inteins, have been suggested (deGray, 2000). The insertion of inteins into such transgenes could reduce the encoded protein's hydrophobicity, thereby enable mitochondrial import followed by post-import excision, which would restore the natural amino acid sequence.

Fourthly, it has been hypothesized that some of the proteins encoded by the mitochondrion may potentially be toxic if synthesized in the cytosol (Jacobs, 1991). Theoretically, inteins might also be useful to interrupt toxic amino acid sequences thus abolishing any cytotoxicity. However, whether inteins are potentially used to "temporarily" reduce either hydrophobicity or cytotoxicity of proteins synthesized in the cytosol and to be imported into mitochondria, a control mechanism has to be found which prevents any pre-imported excision. Suggested strategies to combat this problem involve pH-sensitive inteins, which would only be active at intramitochondrial pH as well as the promotion of co-translational mitochondrial protein import which would prevent the protein from folding into its active conformation and thereby triggering intein excision, before entering mitochondria (deGray, 2000).

The functional expression of an exogeneous gene inside the mitochondria, i.e. via mitochondrial transcription and translation machinery, has so far never been reported. An expression of a functional protein inside the mitochondria requires the construction of an appropriate plasmid, containing both mitochondria-specific regulator sequences and observing mitochondria-specific deviations in the use of the genetic code. An efficient way to deliver plasmid DNA into the mitochondrial matrix still remains to be found.

Years before the need to deliver DNA into mitochondria was recognized, it was shown by Cudd and Nicolau that conventional non-cationic liposomes seem to at least partially associate with liver mitochondria (Cudd et al., 1984, 1985 and 1986). When, for example, liposomes containing uranyl acetate were intravenously injected into mice and hepatocytes isolated one hour later, transmission electron microscopy revealed the presence of liposomes in cytoplasmic vacuoles in the cytoplasm and in association with mitochondria in these cells. They found that an average of one out of ten mitochondria was associated with liposomes. The authors have suggested that a fraction of the liposomes injected intravenously into mice associate with mitochondria in the liver and possibly deliver their aqueous contents there (Cudd et al., 1986). However, neither they nor any other investigators have ever carried out further experiments involving the use of conventional liposomes for the delivery of DNA or other biologically active molecules into mitochondria. Most recently, though, Inoki et al., 2000 have microinjected fluorescence labeled proteoliposomes containing mitochondrial membrane into fertilized mouse eggs. Using confocal laser microscopy they could show the colocalization of these liposomes with endogenous mitochondria, whilst control liposomes composed of soybean phospholipid displayed a subcellular localization different from mitochondria.

Among the first direct attempts to transform mitochondria was the use of the "biolistic" (biological ballistic) gun. However, although foreign DNA has been successfully introduced into mitochondria of yeast by biolistic bombardment of cells with DNA-coated tungsten particles (Butow et al., 1991), this technique has failed so far in mammalian cells.

Another strategy, which can neither be classified as a direct nor as an indirect mitochondrial gene therapy has been developed by Kagawa's laboratory (Kagawa et al., 1997). They demonstrated the correction of a mitochondrial deficiency in a cell model by transfer of "healthy" mitochondria through cytoplast fusion in vitro. Their approach to gene therapy by mitochondrial transfer is described comprehensively in Kagawa et al., 2001.

The biogenesis of mitochondria and their function depends on the coordinated import of precursor proteins from the cytosol. Only a very small set of all mitochondrial proteins, 13 polypeptides that are all part of the protein complexes involved in the oxidative phosphorylation, are being synthesized inside mitochondria. All other proteins must be imported. To this end, both mitochondrial membranes contain an elaborate network of protein translocases together with a variety of chaperones and processing enzymes in the matrix and intermembrane space to mediate protein import. A clear picture of this highly complex mechanism has emerged over the past years and most recently has been reviewed by Lithgow, 2000 and Koehler, 2000. Generally, proteins bearing an amino-terminal targeting sequence, a so-called mitochondrial leader peptide, are escorted through the cytosol by chaperones to the TOM complex, which is a translocase localized in the outer mitochondrial membrane. After crossing the outer membrane, so-called TIM complexes, i.e. translocases of the inner membrane, mediate the further transport into the mitochondrial matrix. Finally, inside the mitochondrial matrix, the leader peptide is cleaved off by a matrix processing protease.

The uptake of exogenous DNA into mitochondria utilizing the protein import pathway has been already reported. Vestweber and Schatz achieved uptake of 24-bp both, single- and double-stranded oligonucleotides into yeast mitochondria by coupling the 5' end of the oligonucleotides to a precursor protein consisting of the yeast cytochrome c oxidase subunit IV presequence fused to a modified mouse dihydrofolate reductase (Vestweber et al., 1989). Seibel et al. reported the import into the mitochondrial matrix of double stranded DNA molecules (17 bp or 322 bp) conjugated to the amino-terminal leader peptide of the rat ornithine transcarbamylase Seibel et al., 1995). The same authors also studied the recognition and cleavage of DNA-peptide conjugates by the endogenous mitochondrial signal peptide processing machinery (Seibel et al., 1999). They demonstrated that artificial peptide-DNA conjugates are recognized by the mitochondrial proteolytic machinery. Therefore, an interference of the peptide with the DNA function seems unlikely (Seibel et al., 1999).

Most recently, Lightowler's group has shown that Peptide Nucleic Acids (PNAs), synthetic DNA-like molecules in which the chains of pyrimidine and purine bases are linked by an amino ethyl backbone, can be partially directed to mitochondria in living cells when conjugated to mitochondria-specific targeting peptides (Chinnery et al., 1999). Intriguingly, their approach may launch the development of anti-sense therapy for disorders of the mitochondrial genome, since the same authors have shown earlier that sequence-specific PNAs selectively inhibit the replication of mutated mtDNA in vitro (Taylor et al., 1999). To test the applicability of their mitochondria-specific anti-sense approach in vivo, the authors have studied the uptake of biotinylated PNAs into cultured cells, using fluorescence confocal microscopy, after staining the fixed cells with streptavidin-fluorescein. Although the PNA ultimately localizes to the nucleus, conjugating the molecule to the presequence peptide of the nuclear-encoded human cytochrome c oxidase subunit VIII directs at least a subset of the molecules to mitochondria. All three studies cited above (Vestweber, Seibel, Chinnery) demonstrate the feasibility of delivering exogenous DNA-peptide conjugates into the mitochondrial matrix by "hitchhiking" through the mitochondrial protein import pathway.

Two principally different strategies can be performed for the detection of exogenous wt-mtDNA that has been transported into mitochondria of living cells via a carrier vehicle. For the physico-chemical or non-functional test, Rho(0) cells, which are cells that completely lack endogenous mtDNA, are used to detect entry of exogenous wt-mtDNA via dot blotting (after lysis of mitoplasts), which employs wt-mtDNA as homologue probe. Thus, no cross hybridization between probe and endogenous mtDNA can occur. For isolation of cells depleted from mtDNA, cells will be grown in the presence of ethidium bromide. Cells cultured with ethidium bromide lose their mtDNA, limiting their ability to carry out oxidative phosphorylation. They would require pyruvate and uridine for growth and have glycolysis as their only source of ATP (King et al., 1989, 1988 and 1996). However, mitochondria are still essential for rho(0) cells. Vital metabolic pathways are catalyzed by mitochondrial proteins, which are encoded by chromosomal DNA, and taken up by mitochondria after their synthesis at cytosolic ribosomes. The import of nuclear-encoded proteins into mitochondria requires a mitochondrial membrane potential. The maximum value of this potential, thought to arise from the electrogenic exchange of $ATP^{4-}$ for $ADp^{3-}$ by the adenine nucleotide carrier, was recently determined to lie between 110 and 67 mV (Appleby et al., 1999), which is according to the Nernst equation sufficient for a more than ten-fold accumulation of mitochondriotropic molecules inside the mitochondrial matrix. Therefore, mitochondria in rho(0) cells are able to "attract," for example, DQAsomes based on the accumulation of cationic amphiphile with delocalized charge center at and in mitochondria in response to the mitochondrial membrane potential.

For isolating rho(0) PC3 prostate carcinoma cells (alternatively, LS-174T Colon Adenocarcinoma cells), the protocol described by Appleby et al., 1999 is used. (The isolation of rho(0) tumor cells is most recently described by Hu et al., 2000.) Cells are grown in Dulbecco's modified Eagle's medium (DMEM)/10% fetal calf serum supplemented with ethidium bromide (100 µg/ml). The depletion of endogenous mtDNA is controlled by Southern hybridization (Sambrook et al., 1989) using isolated wt-mtDNA as homologue probe. Radio labeling of the DNA, southern blotting and autoradiography of the blots will be carried out as described in Wessig et al., 1997 and 1999. The resulting rho(0) cells lacking mtDNA are cultured in DMEM/10% fetal calf serum supplemented with glucose (4.5 g/L), streptomycin sulfate (100 mg/L), penicillin G (100,000 U/L), uridine (50 mg/L) and pyruvate (100 mg/L).

Alternatively, the delivery of wt-mtDNA into normal living cells, i.e., cells containing endogenous mtDNA, is tested using, e.g., DQAsomes. The wt-mtDNA to be transported to and into mitochondria via DQAsomes has to be labeled, either with gold or with ethidium azide, which can then be detected utilizing electron microscopy and confocal fluorescence microscopy, respectively.

For a functional assay to detect the delivery of wt-mtDNA delivered into rho(0) and rho(−) cells, the biological activity of the delivered mtDNA is measured. Cell lines with mutant mtDNA generally display deficient respiration and reduced ATP production, which is linked to a decrease of the mitochondrial membrane potential. Therefore, the membrane potential of mitochondria and the oxygen consumption of these cells, before and after transfection with wt-mtDNA, are measured.

For utilizing the mitochondrial protein import machinery for introducing wt-mtDNA into mitochondria, the DNA has to be conjugated to a MLS peptide. Human wt-mtDNA can be isolated in quantity from tissue culture cells. To obtain a sufficiently large amount of mtDNA, spinner culture cells are used for the required scale up. For conjugation of the mtDNA with an MLS peptide, pGeneGrip™ technology is preferably applied using standard protocols (Sambrook et al., 1989) including protocols obtainable from the manufacturer of the GeneGrip oligonucleotide (GTS, Inc., see also www.genetherapysystems.com). Generally, the method employed in the GeneGrip technology takes a peptide nucleic acid (PNA) oligonucleotide analog that carries chemically reactive groups suited for the covalent coupling of MLS peptides. This analog is hybridized in a sequence-dependent manner to its complementary DNA target (the "101 bp DNA snippet"), which has been inserted into the circular mtDNA molecule prior to adding the PNA oligonucleotide. Subsequently, the MLS peptide is reacted with a maleimide residue of the PNA oligonucleotide via the sulf-hydryl group of an N-terminal cysteine residue.

The overhanging 5' and 3' single DNA strands (sticky ends) of the 101 bp GeneGrip site fragment are compatible with Bam HI or Bgl II restriction sites as manufactured. However, one of ordinary skill in the art can modify the ends of the 101 bp fragment by well known methods to be compatible with other restriction sites. A restriction map of the entire published human mtDNA sequence (e.g., as disclosed in Anderson et al., 1981) can be generated for any desired restriction enzyme using the GCG software MAP. For the experiments reported herein, the restriction map for the Bam HI and Bgl II restriction enzymes was generated. It was found that Bam HI cuts human mtDNA only once, which allows the insertion of the GeneGrip oligonucleotide without further disruption of the integrity of the DNA. There is no restriction site for Bgl II on human mtDNA.

While an ordinary skilled artisan can test many restriction enzymes for an appropriate restriction site to be used in the mtDNA, a preferred enzyme is one that cuts the circular mtDNA only once and maintains the integrity of the mtDNA. Preferably, the restriction site is located in a non-coding region suitable for the insertion of the oligonucleotide that anchors the MLS peptide to the mtDNA. For example, a suitable site is at the "membrane attachment site" from nucleotide position 15925 to nucleotide position 499 of the mtDNA or at the D-Loop region from nucleotide position 16024 to nucleotide position 576 of the mtDNA. See MitoMap for Mitochondrial DNA Function Locations, http://infinity.gen.emory.edu/cgi-bin/MITOMAP/bin/tbllgen.pl.

In addition, complete transcription (early at the heavy strand, late at the light strand) as well as reduplication of the circular DNA will be prevented by the presence of the pGeneGrip™ PNA clamp at position 14258, bearing the maleimide residue with the attached MLS peptide. Although it could be shown that mitochondrial signal peptidases are able to cleave off the peptide attached to DNA (Jacobs, 1991), the maleimide PNA clamp will stay hybridized to the mtDNA. The conjugation of mtDNA with MLS peptides while maintaining the functionality of the DNA is based on the presence of a natural protein-binding site at mtDNA. Albring et al. (1977) have shown that about 95% of mtDNA molecules released by Triton X100 lysis of HeLa cell mitochondria in the presence of 0.15 M salt are associated with a single protein-containing structure varying in appearance between a 10-20 nm knob and a 100-500 nm membrane-like patch. This protein structure is attached to the DNA in the region of the D-loop and mediates the attachment of mtDNA to the inner mitochondrial membrane (Albring et al., 1977 and Wallace et al., 1995). Sac I cuts at np 40, which is inside this membrane attachment site (np 15925-499). Sac I cuts also at np 9647, which disrupts the gene for cytochrome c oxidase III (np 9207-9990). In addition, the sticky ends of the GeneGrip oligonucleotide are not compatible with Sac I. However, these obstacles will be overcome by blunt end ligation.

Alternatively, LabelIT technology (via Mirus) for the conjugation of MLS peptides to wild-type mtDNA can be used. The simpler approach of this technology appears as an advantage over GeneGrip technology. However, a disadvantage of this method may be the attachment of the peptides at random sites of the mtDNA.

Measuring the mitochondrial membrane potential provides a determinant for the validity of the functionality of the imported mtDNA. Measurement of mitochondrial membrane potential on, cell suspensions is described in Lemasters et al. (1993). A widely used standard procedure for measuring mitochondrial membrane potentials is to measure the equilibrium distribution of membrane-permeant cation probes. Positively charged molecules are taken up by mitochondria in response to the high negative membrane potential. Organic compounds with delocalized charge can cross the mitochondrial membrane in response to the membrane potential. One of the most commonly used probes is rhodamine 123. The uptake of rhodamine 123 into the mitochondria of cell suspensions can be easily assessed by centrifuging the cells and measuring rhodamine 123 associated with the pellet as follows: Cells are suspended in modified Krebs-Ringer-HEPES (KRH) buffer containing 1 µM rhodamine 123. After different time points, 3 ml aliquots are centrifuged at 700 rpm for 2 minutes in a table top centrifuge. The supernatant is removed, and the pellet containing the cells are resuspended in KRH containing 0.1% (v/v) Triton X-100. The detergent serves to lyse the cells and to release all rhodamine 123 they contain. After 10 minutes, samples are centrifuged again at 3500 rpm for 2 minutes to sediment any cellular debris. The rhodamine 123 concentration in the supernatant is measured with a fluorescence spectrophotometer at excitation 490 and emission 515 nm. The retention of rhodamine is used as a measure for the difference in the membrane potential of the mtDNA mutant parent cell line versus cell transfected with mitochondrial wild-type DNA.

As an alternative method, the retention of rhodamine 123 in mitochondria inside living cells in response to the mitochondrial membrane potential can also be measured by flow cytometric analysis as described recently in Hu et al., 2000. Cells are treated with rhodamine 123 at 0.01 mg/ml for 10 minutes, then rinsed and incubated in rhodamine 123 free medium for 4 hours. At this time, cells are removed immediately by a rubber policeman and analyzed by FACScan flow cytometry (see description above). With this method, Hu et al., 2000 found that rho(0) cells retained four times less rhodamine 123 than wild-type cells.

Measuring mitchondrial respiration is another means of determining successful uptake of wt-mtDNA into a mitochondrion. Measurement of the mitochondrial respiration (oxygen consumption) is determined using the methods described in Rickwood et al., 1987Mitochondrial respiration can be most conveniently and quickly measured using a "Clarke" type oxygen electrode (Rickwood et al., 1987). A detailed description for setting up and calibrating the electrode is provided in Rickwood et al., 1987. However, a drawback of this method is the need for isolating the mitochondria from the cell cultures before the oxygen consumption can be measured. Therefore, this method is useful only in cases where unexpected difficulties are encountered with the assay described above for rhodamine 123 retention. The general procedure constitutes adding isolated mitochondria (for appropriate isolation protocol see above) to 2.4 ml isolation medium in the oxygen electrode followed by glutamate/malate to a final concentration of 2.5 mM. The oxygen uptake is recorded for a few minutes and then ADP to a final concentration of 0.18 mM is added. The oxygen uptake in response to the addition of ADP is measured and compared between rho(0) or rho(-) cells and the wild-type mtDNA treated cells. Reduced oxygen uptake will indicate a reduced respiration.

The following additional examples are presented to illustrate the advantages of the present invention and to assist one of ordinary skill in making and using the same. These examples are not intended in any way otherwise to limit the scope of the disclosure.

EXAMPLE I

Carrier Vehicle Mediated Intracellular Uptake of Mitochondrial DNA

The intracellular distribution of internalized DQAsome/DNA complexes with mitochondrial DNA (mtDNA) is studied using the following protocols. BT20 cells are grown on 22 mm circular cover slips in 6 well cell culture plates until they are approximately 60-80% confluent followed by incubation in serum free medium for 1 h with the DQAsome/DNA complex. For control, cells are exposed to naked DNA and empty DQAsomes, respectively. After removing the medium containing non-internalized material, cells are thoroughly washed and grown for 4 h in complete medium. Thereafter, cells are incubated consecutively with Mitotracker Red CMXRos for staining mitochondria and with SYBR Green I for staining free DNA. Since SYBR shows fluorescence only upon interaction with free DNA, this method shows mtDNA that is already released from the internalized DQAsome/DNA complex, i.e., accessible to the fluorescence dye. It should be stressed that the DQAsome/DNA complexes used for these studies are prepared after the DNA binding capacity of each DQAsome preparation is determined in order to choose the correct DQAsome:DNA ratio, thereby excluding the presence of any excess of free mtDNA.

This study is a successful approach based on the experiments involving plasmid DNA (pDNA) by the inventors. Based on a similar study using pDNA, the transport of PDNA by DQAsomes to the site of mitochondria and released from the DQAsome/DNA complex upon contact with the mitochondrial membrane was achieved. The results indicated that SYBR Green I stained the cell nucleus in untreated control cells and in cells incubated with empty DQAsomes and with naked pDNA. Hardly any fluorescence was detectable in the cytosol. In contrast, in cells incubated with DQAsome/DNA complex, spots of intense SYBR fluorescence appear outside the nucleus, indicating internalized mtDNA which was already accessible to the fluorescence dye, i.e., which was released from the internalized DQAsome/DNA complex. A comparison of the SYBR stained image with the corresponding Mitotracker image strongly suggests that the internalized DQAsome/DNA complexes release the DNA at the site of mitochondria.

These results are relevant for the mitochondrial genome replenishment since they prove the delivery of circular DNA to the site of mitochondria in the cytosol of living cells.

EXAMPLE II

Optimal Conditions for Selectively Staining Free Mitochondrial DNA Released into the Cytosol Using SYBR Green I For visualizing mitochondrial DNA transported to mitochondria in living cells and released from the DQAsome/DNA complex upon contact with mitochondrial membranes, conditions are studied to determine whether or not the dye enters mitochondria and, hence, whether or not it stains endogenous mitochondrial DNA. Cells were stained for 5 minutes with Mitotracker (for mitochondria) and SYBR (for free DNA). The comparison of both images, showing co-stained identical cells, demonstrated that SYBR Green I was exclusively confined to the nucleus and did not enter mitochondria.

However, if cells are incubated with SYBR for an extended period of time, e.g., for 20 minutes, the dye is able to access endogenous mitochondrial DNA. It was demonstrated that seemingly all mitochondria display green fluorescence. The difference in the fluorescence intensity between the nuclei and the mitochondria can be explained by the mass ratio between mtDNA and nuclear DNA (mtDNA about 1% of total DNA).

EXAMPLE III

Confocal Fluorescence Study of Delivery of Mitochondrial DNA to Mitochondrion of a Cell BT20 cells are grown on 22 mm circular cover slips in 6 well cell culture plates until they are approximately 60-80% confluent followed by incubation in serum free medium for 1 h with the DQAsome/DNA complex. For control, cells are exposed to naked DNA and empty DQAsomes, respectively. After removing the medium containing non-internalized material, cells are thoroughly washed with CellScrub buffer and grown for 4 h in complete medium. Thereafter, cells are incubated consecutively with Mitotracker Red CMXRos for staining mitochondria and with SYBR Green I for staining free DNA. Cells are then analyzed by confocal fluorescence microscopy.

Using confocal fluorescence in a pDNA study, green fluorescence indicates PDNA and red fluorescence indicates mitochondrion. The circular plasmid DNA (green fluorescence) was transported by DQAsomes into the cytosol to the site of mitochondria (red fluorescence). Since SYBR produces a green fluorescence signal only when interacting with DNA, which in turn has to be accessible to the dye, we concluded that plasmid DNA was dissociated from the DQAsome/DNA complex. The results showed that the green fluorescence (free DNA) co-localized with mitochondria (red). The dissociation of the DNA from the DQAsome/DNA complex occurred upon contact with the mitochondrial membrane.

In sum, these studies show in a direct way that DQAsomes not only mediate the cellular uptake of pDNA, but also possible to transport mtDNA into the cytosol to the site of mitochondria. In addition, the confocal fluorescence images also demonstrate that DQAsome/DNA complexes released DNA upon contact with mitochondrial membranes. While the size ratio of pDNA to mtDNA is about 1:3, one of ordinary skill in the art can appreciate that because of the supercoil form of the mtDNA, the results from the pDNA work and other earlier work with linear fragments can be analogously applied. With these studies, the uptake of a wt-mtDNA conjugated to a MLS peptide by the mitochondrial protein import machinery provides a novel approach as a therapeutic agent in treating conditions attributed to mitochondrial defects.

Use

The delivery of a wild-type mitochondrial DNA molecule of the invention is useful for a variety of applications including treating a patient having a condition attributed to a mitochondrial DNA defect. Mitochondrial DNA (mtDNA) defects include, but are not limited to, a mtDNA point mutation, a deletion or a duplication, multiple deletions and a depletion. Disorders associated with a point mutation include, but are not limited to, cardiomyopathy, Leber's optic neuropathy, Leigh's syndrome, MELAS, MERRF and NARP/MILS. A deletion or a duplication associated disorders include, e.g., ataxia, leukodystrophy, diabetes (maternal inheritance), Kearns-Sayre and Pearson's, progressive external ophthalmoplegia (PEO) (sporadic). A multiple deletion associated disorders include aging, myositis, inclusion-body myositis, COX-muscle fibers myositis, MNGIE, PEO and Wolfram. Aging related disorders include, such as, Parkinson's, arteriosclerosis, arthritis, diabetes and Alzheimer's. Depletion of mtDNA associated disorders and causes include, for example, infantile myopathy, fatal infantile myopathy, later-onset infantile myopathy and AZT treatment. Other mtDNA defects, include, but are not limited to, deafness, diabetes, external ophthalmoplegia (PEO) (sporadic, maternal, dominant, recessive), Leigh's, myopathy, rhabdomyolysis, sensory neuropathy and systemic disorders. (For a more comprehensive list, see also, Pulkes et al., 2001; www.neuro.wustl.edu/neuromuscular/mitosyn.html; and www.gen.emory.edu/mitomap.html.)

Such treatment may be administered either topically or systemically using the carrier vehicle described above. Topical administration may include, but is not limited to, intramuscular, intraperitoneal, intracerebral or intraspinal injection. Systemic administration may include, but is not limited to, intravenous injection and oral ingestion.

Systemic administration, in vivo, of some mitochondriotropic carrier vehicle/DNA-MLS-peptide complexes might require a particular shielding mechanism. Since, for example, DQAsome/DNA-MLS-peptide complex is positively charged, it will easily interact with several blood components such as opsonins, resulting in the early and rapid clearance of the complex from the blood circulation. The positive charge of the DQAsome/DNA complex can be shielded by covalent attachment of polyethylene glycol (PEG). It was shown by Ogris et al. (1999) that shielding DNA/PEI (polyethylene imine) complexes with PEG can prevent the unspecific interaction with blood compounds but does not interfere with the target cell specific interaction. Accordingly, DQAsomes can be prepared in the presence of 5 mol % 1,2-Diacyl-sn-glycero-3-phosphoethanolamine-N-[Methoxy(Polyethylene glycocl)-5000] (PEG5000-PE). The hydrophilic and protecting PEG chain is anchored in the hydrophobic bilayer of DQAsomes via the hydrophobic phospholipid residue, as it is well known from Liposome Technology. PEG-DQAsomes so obtained can then be complexed with the mitochondrial DNA and are ready for intravenous administration.

Depending on the frequency and route of administration, the therapeutic compositions of the invention can be administered in a dosage of 0.25 µg/kg/day to 10 mg/kg/day, and preferably 5 mg/kg/day. In a bolus form, the composition of the invention can be administered in a dosage of 5 mg/kg/day to 20 mg/kg/day, preferably 12 mg/kg/day. Optimal dosage and modes of administration can readily be determined by conventional protocols.

The therapeutic compositions of the invention can be administered independently or co-administered with another appropriate therapeutic agent.

Replenishment of defective mtDNA with a wild-type mtDNA molecule in accordance with the invention is a novel approach to mitochondrial gene therapy that treats conditions attributed to mtDNA defects on a permanent basis.

REFERENCES

Alberts et al. (1994) Molecular Biology of the Cell. 3$^{rd}$ edition, Garlent Publishing Inc., NY and London, p.569;

Albring et al. (1977) "Association Of A Protein Structure Of Probable Membrane Derivation With Hela Cell Mitochondrial DNA Near Its Origin Of Replication", Proc. Natl. Acad. Sci., 74:1348-1352;

Anderson et al. (1981) "Sequence And Organization Of The Human Mitochondrial Genome", Nature, 290:457-465;

Appleby et al. (1999)"Quantitation And Origin Of The Mitochondrial Membrane Potential In Human Cells Lacking Mitochondrial DNA", Eur. J. Biochem., 262:108-116;

Bigger et al. (2000) "Introduction Of Chloramphenicol Resistance Into The Modified Mouse Mitochondrial Genome: Cloning Of Unstable Sequences By Passage Through Yeast", Anal. Biochem, 277:236-242;

Barrell et al. (1979) "Different Genetic Code In Human Mitochondria", Nature, 282:189-194;

Butow et al. (1991) "Organelle Transformation: Shoot First, Ask Questions Later", Trends Biochem. Sci., 15:465-468;

Chinnery et Al (1999) "Peptide Nucleic Acid Delivery To Human Mitochondria", Gen Therapy, 6:1919-1928;

Chrzanowska-Lightowlers et al. (1995) "Gene Therapy For Mitochondrial DNA Defects: Is It Possible?", Gene Therapy, 2:311-316;

Collombet et al. (1997) "Introduction Of Plasmid DNA Into Isolated Mitochondria By Electroporation. A Novel Approach Towards Gene Correction For Mitochondrial Disorders", J. Biol. Chem., 272:5342-5347;

Collombet et al. (1998) "Towards Gene Therapy Of Mitochondrial Disorders", Molecular Medicine Today, 4:883-890;

Conary et al. (1995) "Compositions For And Methods Of Enhancing Delivery Of Nucleic Acids To Cells", WO 95/34647; PCT/US95/07543;

Cudd et al. (1984) "Liposomes Injected Intravenously Into Mice Associate With Liver Mitochondria", Biochim. Biophys. Acta, 774:169-180;

Cudd et al. (1985) "Intracellular Fate Of Liposome-Encapsulated DNA In Mouse Liver. Analysis Using Electron Microscope Autoradiography And Subcellular Fractionation", Biochim. Biophys. Acta, 845:477-491;

Cudd et al. (1986) "Interaction Of Intravenously Injected Liposomes With Mouse Liver Mitochondria. A Fluorescence And Electron Microscopy Study", Biochim. Biophys. Acta, 860:201-214;

Degray (2000) "Mitochondrial Gene Therapy: An Arena For The Biomedical Use Of Inteins", Trends Biotechnol., 18:394-399;

De Vivo (1993) "Mitochondrial DNA Defects: Clinical Features", Mitochondrial DNA In Human Pathology (Dimauro et al., Eds.), Raven Press, N.Y., Pp. 39-52;

Entelis et al. (2001) "RNA Delivery Into Mitochondria", Adv. Drug Deliv. Rev., 49:199;

Gregoriadis (Eds.) (2000) "Targeting Of Drugs: Strategies For Gene Constructs And Delivery", IOS Press, Amsterdam, Berlin, Oxford, Tokyo, Washington, D.C.;

Harding (1991) "Neurological Disease And Mitochondrial Genes", TINS, 14:132-138;

Hauswirth et al. (1987) "Methods For Studying The Genetics Of Mitochondria", In: 45:171-244;

Holt et al. (1988) "Deletions Of Muscle Mitochondrial DNA In Patients With Mitochondrial Genes", Nature, 331:717-719;

Hu et al. (2000) "Rho(0) Cells: A Model For Studying Whether Mitochondria Are Targets For Rhodamine 123, Doxorubicin, And Other Drugs", Biochemical Pharmacology, 60:1897-1905;

Inoki et al. (2000) "Proteoliposomes Colocalized With Endogenous Mitochondria In Mouse Fertilized Egg", Biochem. Biophys. Res. Commun., 278:183-191;

Jacobs (1991) "Structural Similarities Between A Mitochondrially Encoded Polypeptide And A Family Of Prokaryotic Respiratory Toxins Involved In Plasmid Maintenance Suggest A Novel Mechanism For The Evolutionary Maintenance Of Mitochondrial DNA", J. Mol. Evol. 32:333-339;

Kagawa et al. (1997) "Gene Therapy Of Mitochondrial Diseases Using Human Cytoplasts", Gene Ther., 4:6-10;

Kagawa et al. (2001) "Gene Therapy By Mitochondrial Transfer", Adv. Drug Deliv. Rev., 49:107;

King et al. (1988) "Injection Of Mitochondria Into Human Cells Leads To A Rapid Replacement Of The Endogeneous Mitochondrial DNA", Cell, 52:811-819;

King et al. (1989) "Human Cells Lacking Mtdna; Repopulation With Exogenous Mitochondria By Complementation", Science, 246:500-503;

King et al. (1996) "Isolation Of Human Cell Lines Lacking Mitochondrial DNA", Methods Enzymol., 264:304-313;

Koehler (2000) "Protein Translocation Pathways Of The Mitochondrion", FEBS Lett., 476:27-31;

Kolesnikova et al. (2000) "Suppression Of Mutations In Mitochondrial DNA By Trnas Imported From The Cytoplasm", Science 289:1931-1933;

Ledley (1996) "Pharmaceutical Approach To Somatic Gene Therapy", Pharm. Res. 13:1595-1614;

Lemasters et al. (1993) "Use Of Fluorescent Probes To Monitor Mitochondrial Membrane Potential In Isolated Mitochondria, Cell Suspensions And Cultured Cells, In: Mitochondrial Dysfunction, Lash et al. (Eds), Methods In Toxicology, Vol. 2, Academic Press, Inc., San Diego, New York, Boston, London, Sydney, Tokyo, Toronto, 1993;

Lithgow (2000) "Targeting Of Proteins To Mitochondria", FEBS Lett., 476:22-26;

Nagley et al. (1988) "Assembly of Functional Proton Translocating ATPase Complex in Yeast Mitochondria with Cytoplasmically Synthesized Subunit 8, a Polypeptide Normally Encoded within the Organelle. PNAS USA, 85:2091-2095;

Ogris et al. (1999) "PEGylated DNA/Transferrin-PEI complexes: Reduced interaction with blood components extended circulation in blood and potential for systemic gene delivery." Gene Therapy 6:595-605;

Owen IV et al. (2000) "Recombinant Adeno-Associated Virus-Based Gene Transfer For Defects In Oxidative Metabolism", Hum. Gene Ther. 11:2067-2078;

Papa et al. (1996) "Mitochondrial Diseases And Aging", Mol. Asp. Medicine, 17:513-563;

Pulkes et al. (2001) "Human Mitochondrial DNA Diseases", Adv. Drug Deliv. Rev.—Theme Issue "Drug And DNA Delivery To Mitochondria" (Weissig et al., Eds), 49:27-43;

Rickwood et al. (1987) "Isolation And Characteristics Of Intact Mitochondria, In: Mitochondria—A Practical Approach, Darley-Usmar et al. (Eds.), IRL Press, Oxford, Washington D.C. (1987), Pp. 11-14;

Rolland et Al (Ed.) (1999) "Advanced Gene Delivery", Harwood Academic Publishers, Amsterdam;

Sambrook et al. (1989) "Molecular Cloning, A Laboratory Manual, $2^{nd}$ Ed." (Cold Spring Harbor, N.Y.: Cold Spring Harbor Laboratory Press);

Schneider (1994) "Import Of RNA Into Mitochondria", Trends In Cell Biology, 4:282-286;

Scheffler (1999) "Evolutionary Origin Of Mitochondria" I. E. Scheffler, Mitochondria, Wiley-Liss, A John Wiley & Sons, Inc., Publication, New York, Chichester, Weinheim, Brisbane, Singapore, Toronto, Pp. 7-14;

Seibel et al. (1995) "Transfection Of Mitochondria: Strategy Towards A Gene Therapy Of Mitochondrial DNA Diseases", Nucleic Acid Res., 23:10-17;

Seibel et al. (1999) "Processing Of Artificial Peptide-DNA-Conjugates By The Mitochondrial Intermediate Peptidase", Biol. Chem., 380:961-967;

Sewards et al. (1994) "Apparent Functional Independence Of The Mitochondrial And Nuclear Transcriptionsystems In Cultured Human Cells", Mol. Gen. Genet., 245:760-768;

Sobol et al. (Eds.) (1995) "The Internet Book Of Gene Therapy", Appleton & Lange, Stamford, Conn.;

Taylor et al. (2001) "An Antigenomic Strategy For Treating Heteroplasmic MtDNA Disorders", Adv. Drug Deliv. Rev. 49:121-125;

Taylor et al. (1997) "Selective Inhibition Of Mutant Human Mitochondrial DNA Replication In Vitro By Peptide Nucleic Acids", Nature Genet, 15:212-215;

Vestweber et al. (1989) "DNA-Protein Conjugates Can Enter Mitochondria Via The Protein Import Pathway", Nature, 388:170-172;

Wallace et al. (1988) "Mitochondrial DNA Mutation Associated With Leber's Hereditary Optic Neuropathy", Science, 242:1427-1430;

Wallace et al. (1995) "Report Of The Committee On Human Mitochondrial DNA. In Cuticchia, A. J. (Ed), Human Gene Mapping 1995: A Compendium. John Hopkins University Press, Baltimore, Pp. 910-954 (Available At Http://Www.Gen.Emory.Edu/Mitomap.Html)

Wallace (1999) "Mitochondrial Diseases In Man And Mouse", Science, 283:1482-1488;

Weissig et al. (1997) "Topoisomerase II Inhibitors Induce Cleavage Of Nuclear And 35-Kb Plastid Dnas In The Malarial Parasite Plasmodium Falciparum", DNA And Cell Biology, 16:1483-1492;

Weissig et al. (1999) "Analysis Of P. Falciparum Mitochondrial 6 Kilobase DNA By Pulse-Field Electrophoresis", J. Parasitology, 85:386-389; and Wheeler et al. (1997) "Insertion Of An Exogenous Gene Into The Mouse Mitochondrial Genome By Homologous Recombination In Yeast", Gene, 198:203-209.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A composition for delivering a wild-type mitochondrial DNA genome to a mammalian cell, said composition comprising:
   a wild-type mammalian mitochondrial DNA genome molecule;
   a mitochondrial leader sequence peptide attached to said mitochondrial DNA genome molecule; and
   a carrier vehicle comprising two delocalized cationic centers separated by a hydrocarbon chain.

2. The composition of claim 1, wherein said mitochondrial leader sequence peptide is attached in a non-coding region.

3. The composition of claim 1, wherein said mitochondrial leader sequence peptide is attached in a region of the membrane attachment site from nucleotide position 15925 to nucleotide position 499 of said mitochondrial DNA genome molecule.

4. The composition of claim 1, wherein said mitochondrial leader sequence peptide is attached in a region of the D-loop from nucleotide position 16024 to nucleotide position 576 of said mitochondrial DNA genome molecule.

5. The composition of claim 1, wherein said wild-type mammalian mitochondrial DNA genome molecule originates from a mammalian cell.

6. The composition of claim 1, wherein said wild-type mammalian mitochondrial DNA genome molecule is isolated from cell culture.

7. The composition of claim 1, wherein said wild-type mammalian mitochondrial DNA genome molecule is chemically synthesized.

* * * * *

UNITED STATES PATENT AND TRADEMARK OFFICE
CERTIFICATE OF CORRECTION

PATENT NO. : 7,279,326 B2  Page 1 of 1
APPLICATION NO. : 10/485407
DATED : October 9, 2007
INVENTOR(S) : Volkmar Weissig et al.

It is certified that error appears in the above-identified patent and that said Letters Patent is hereby corrected as shown below:

Column 7, line 54, "$AD_p^{3-}$" should read --$ADP^{3-}$--;

Column 9, line 47, "on," should read --on--;

Column 10, line 23, "1987Mitochondrial" should read --1987. Mitochondrial--; and Column 12, line 8, "PDNA" should read --$_p$DNA--.

Signed and Sealed this

Twelfth Day of May, 2009

JOHN DOLL
*Acting Director of the United States Patent and Trademark Office*